(12) United States Patent
Kim et al.

(10) Patent No.: US 9,487,770 B2
(45) Date of Patent: Nov. 8, 2016

(54) RECOMBINANT CELLULASE AND USE THEREOF

(71) Applicant: Korea University Research and Business Foundation, Seoul (KR)

(72) Inventors: Kyoung Heon Kim, Seoul (KR); In-Geol Choi, Seoul (KR); Hee Jin Lee, Seoul (KR); In Jung Kim, Gyeongsangbuk-do (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 14/786,711

(22) PCT Filed: Apr. 25, 2014

(86) PCT No.: PCT/KR2014/003665
§ 371 (c)(1),
(2) Date: Oct. 23, 2015

(87) PCT Pub. No.: WO2014/175701
PCT Pub. Date: Oct. 30, 2014

(65) Prior Publication Data
US 2016/0097043 A1  Apr. 7, 2016

(30) Foreign Application Priority Data

Apr. 26, 2013 (KR) .......................... 10-2013-0046423
Apr. 25, 2014 (KR) .......................... 10-2014-0050018

(51) Int. Cl.
*C12N 9/24* (2006.01)
*C12N 9/42* (2006.01)
*C12P 19/02* (2006.01)
*C12P 19/14* (2006.01)

(52) U.S. Cl.
CPC ............. *C12N 9/2437* (2013.01); *C12P 19/02* (2013.01); *C12P 19/14* (2013.01); *C12Y 302/01004* (2013.01)

(58) Field of Classification Search
CPC ................................... C12N 9/00; C12N 9/24
See application file for complete search history.

(56) References Cited

U.S. PATENT DOCUMENTS

| 7,365,180 B2 | 4/2008 | Taylor et al. |
| 2012/0115235 A1 | 5/2012 | Hutcheson |
| 2013/0084619 A1 | 4/2013 | Bayer et al. |

FOREIGN PATENT DOCUMENTS

| KR | 10-0423670 B1 | 3/2004 |
| KR | 10-2006-0011675 A | 2/2006 |
| KR | 10-1137020 B1 | 4/2012 |
| KR | 10-1218341 B1 | 1/2013 |
| WO | 9634108 A2 | 10/1996 |

OTHER PUBLICATIONS

Lee et al., Journal of Biotechnology, vol. 136, Supplement, Oct. 2008, p. S343.*
NCBI, Reference Sequence: YP_435061.1 (Dec. 22, 2012), found at http://www.ncbi.nlm.nih.gov/nuccore/435061.

* cited by examiner

*Primary Examiner* — Maryam Monshipouri
(74) *Attorney, Agent, or Firm* — Fox Rothschild LLP (57) ABSTRACT

The present invention provides *Hahella chejuensis*-derived recombinant cellulase and a use thereof. The recombinant cellulase according to the present invention has a high stability at a high temperature and an optimized activity at a neutral pH, and therefore has a high availability in a process. Also, since the cellulase according to the present invention has an exoglucanase activity as well as an endoglucanase activity, a monosaccharide can be produced during decomposition of cellulose and an additional treatment required in a fermentation process is not needed, and therefore a cost may be reduced. Such an enzyme activity is advantageous to a fermentation or thermal treatment condition for producing a biofuel, and therefore industrial profits may be achieved.

11 Claims, 6 Drawing Sheets

RECOMBINANT CELLULASE AND USE THEREOF

CROSS-REFERENCE TO RELATED APPLICATIONS

This application is the U.S. National Phase of International Application No. PCT/KR2014/003665, filed Apr. 25, 2014, which claims the priority of Korean Application Nos. 10-2013-0046423, filed Apr. 26, 2013 and 10-2014-0050018, filed Apr. 25, 2014, the disclosures of which are all incorporated herein by reference.

TECHNICAL FIELD

The present invention relates to a *Hahella chejuensis*-derived recombinant cellulase and a use thereof.

BACKGROUND ART

To solve problems of instability of an oil price due to a limited crude oil resource and global warming, the world has focused on developing new alternative energy. Accordingly, biofuels including bioethanol capable of being produced from a regenerable plant resource have greatly attracted attention.

A regenerable plant resource, biomass, mostly consists of a lignocellulose type. Here, the lignocellulose mainly consists of cellulose and hemicellulose as a carbohydrate, and lignin. Among these, the cellulose is hydrolyzed with a cellulase, thereby obtaining a sugar such as glucose which can be easily fermented by a microorganism, and the sugar will be converted into a biofuel through fermentation later.

However, the lignocellulose is difficult to be saccharified because, unlike a sucrose-based or starch-based biomass, cellulose is surrounded by hemicellulose and lignin. Generally, a cellulose hydrolysis conversion by cellulases is about 20% of a theoretical maximum. For this reason, it is necessary to perform a physicochemical pretreatment, and pretreated lignocellulose still needs a large amount of the cellulase. Therefore, to achieve an efficient saccharification of pretreated lignocellulose, it is important to increase an activity of the cellulase. Particularly, since the pretreatment is performed at a high temperature, it is very important to ensure a cellulase having stability even at the high temperature.

While cellulases having an increased activity have been disclosed in Korean Patent Nos. 10-1218341, 10-1137020, and 10-0423670, a cellulase having a high activity and excellent processivity at a high temperature has not been reported yet.

DISCLOSURE

Technical Problem

The present invention is directed to providing a recombinant cellulase having a high activity even at a high temperature and excellent processivity.

The present invention is also directed to providing a method of decomposing cellulose with the recombinant cellulase.

Technical Solution

To achieve the above-describe objective, the present invention provides a *Hahella chejuensis*-derived recombinant cellulase from which a signal sequence and two CBM6 domains are removed.

The recombinant cellulase of the present invention may include a sequence for facilitating isolation and purification at a terminal. For example, the recombinant cellulase of the present invention may further include a histidine tag at a terminal of a cellulase of *Hahella chejuensis* from which a signal sequence and two CBM6 domains are removed, but the present invention is not limited thereto.

In one exemplary embodiment of the present invention, a *Hahella chejuensis*-derived recombinant cellulase having the amino acid sequence of SEQ ID NO: 1 in the accompanying sequence listing is provided.

The present invention also provides a gene encoding the recombinant cellulase.

In one exemplary embodiment, the gene may include the nucleic acid sequence set forth in SEQ ID NO: 2.

The present invention also provides a recombinant vector expressing the recombinant cellulase.

The present invention also provides a transformant transformed with the recombinant vector.

The present invention also provides a method of producing a cellulase including isolating and purifying a recombinant cellulase from a cell culture of the transformant.

The present invention also provides a composition for decomposing cellulose, which includes the recombinant cellulase.

The present invention also provides a method of decomposing cellulose, which includes reacting the recombinant cellulase with cellulose.

Advantageous Effects

The cellulase of the present invention has a high stability at a high temperature and an optimized activity at a neutral pH, and therefore has a high availability in a process. Also, since the cellulase according to the present invention has an exoglucanase activity as well as an endoglucanase activity, a monosaccharide can be produced during decomposition of cellulose. Thus, an additional saccharification treatment required for a fermentation process is not needed, which reduce the process cost. Such enzymatic characteristics are beneficial for fermentation or thermal treatment condition for producing a biofuel, and industrial application can be achieved.

MODES OF THE INVENTION

The present invention provides a *Hahella chejuensis*-derived recombinant cellulase.

The recombinant cellulase of the present invention is a recombinant cellulase prepared by removing a signal sequence and two CBM6 domains from a *Hahella chejuensis*-derived cellulase (HcCel5H).

The recombinant cellulase of the present invention may include a sequence for facilitating isolation and purification at a terminal. For example, the recombinant cellulase of the present invention may include an additional histidine tag at a terminal of the *Hahella chejuensis*-derived cellulase from which the signal sequence and the two CBM6 domains are removed, but the present invention is not limited thereto.

In one exemplary embodiment, the cellulase may have the amino acid sequence set forth in SEQ ID NO: 1, and all mutants having a desired activity of the present invention obtained by one or more mutations such as substitution, deletion, inversion, and translocation with respect to the corresponding amino acid sequence may also be included in the enzyme of the present invention.

According to an exemplary embodiment, the molecular weight of the cellulase may be about 34 kDa, which is analyzed by SDS-PAGE.

Q2SFD8 (Gene ID: 3842516), which corresponds to the cellulase of *Hahella chejuensis* used as the origin of the recombinant cellulase of the present invention, is originally annotated as an endoglucanase. The protein consists of three main domains, which are a cellulase section and two members of cellulose binding module (CBM) family 6. The recombinant cellulase according to the present invention includes neither a signal sequence nor a CBM6 domain, is isolated and purified through affinity chromatography, and the recombinant cellulose was confirmed as having no difference in activity with respect to substrate or an even higher activity than the original cellulase of *Hahella chejuensis*.

Meanwhile, a test for measuring an activity with respect to temperature and pH was performed on the recombinant cellulase using soluble cellulose, which was carboxy methyl cellulose (CMC), and thereby it was confirmed that optimal activity was shown at pH 6 and 50° C. Also, as the recombinant cellulase was incubated at different temperatures for a certain time and examined whether its activity was destroyed, it was confirmed that a protein kept its activity even at a high temperature (60° C.).

Also, reaction products produced by the reaction with insoluble cellulose, Avicel, were found to be only monosaccharides such as glucose, and disaccharides such as cellobiose, which was confirmed by TLC and HPLC. This shows that the recombinant cellulase according to the present invention has both activities as an endoglucanase and an exoglucanase. Due to such a property, the recombinant cellulase of the present invention may decompose a cellotriose or higher oligosaccharide, for example, cellotriose, cellotetraose, cellopentaose, or cellohexaose.

The recombinant cellulase of the present invention may be produced by a method of synthesizing a peptide, which is known in the art. For example, using a gene cloning and protein expression system or a peptide synthesizer, the recombinant cellulase of the present invention may be produced by an in vitro synthesizing method.

The present invention also provides a gene encoding the recombinant cellulase.

The gene may have the nucleic acid sequence of SEQ ID NO: 2, and in consideration of degeneracy of a genetic code and the mutant protein as described above, a gene having the base sequence of SEQ ID NO: 2 and a homology of 80% or more, specifically, 85% or more may also be included in the scope of the present invention.

The present invention also relates to a recombinant vector expressing the cellulase.

The term "recombinant vector" used herein is a vector capable of expressing a target protein in suitable host cells, and refers to a gene construct having essential regulatory factors operably linked to express a gene insert.

The vector may include, but is not limited to, a plasmid vector, a cosmid vector, a bacteriophage or a virus vector. A suitable expression vector includes a signal sequence or leader sequence for membrane targeting or secretion as well as expression regulatory elements such as a promoter, an operator, a start codon, a termination codon, a polyadenylation signal and an enhancer, and may be constructed in various forms depending on purpose. The promoter of a vector may be constitutive or inducible. Also, the expression vector includes a selective marker for selecting host cells containing a vector, and if it is a replicable expression vector, includes the origin of replication.

The recombinant vector of the present invention may be constructed by inserting a nucleic acid encoding the cellulase into a general vector for expressing an *E. coli* strain, preferably, a pET21 vector. In one exemplary embodiment of the present invention, as the *E. coli* expression vector, pET21 was used, but the present invention is not limited thereto, and therefore all of the generally used expression vectors for an *E. coli* strain can be used without limitation. In one exemplary embodiment of the present invention, the recombinant vector may be constructed by inserting a DNA fragment including the cellulase-encoding gene (SEQ ID NO: 2) of the present invention using the expression vector for an *E. coli* strain, which is the pET21 vector.

The present invention also relates to a transformant transformed with the recombinant vector.

The transformation includes any method for introducing a nucleic acid into an organism, cell, tissue or organ, and may be carried out by selecting a suitable standard technique depending on a host cell as known in the art. Such a method may be, but is not limited to, electroporation, protoplast fusion, calcium phosphate ($CaPO_4$) precipitation, calcium chloride ($CaCl_2$) precipitation, stirring with silicon carbide fibers, *Agrobacterium*-mediated transformation, PEG, dextrane sulfate, lipofectamine, etc.

Also, since an expression level and modification of a protein may vary depending on a host cell, a most suitable host cell may be selected depending on purpose.

The host cells may be, but are not limited to, prokaryotic host cells derived from *Escherichia coli, Bacillus subtilis, Streptomyces, Pseudomonas, Proteus mirabilis* or *Staphylococcus*. The host cells may also be lower eukaryotic cells such as a fungi (for example, *Aspergillus*) or a yeast (for example, *Pichia pastoris, Saccharomyces cerevisiae, Schizosaccharomyces, Neurospora crassa*), or higher eukaryotic cells such as plant cells.

The transformant may be easily produced by introducing the recombinant vector into arbitrary host cells. According to an exemplary embodiment of the present invention, the transformant may be produced by introducing the recombinant vector pET21 expressing a cellulase into the *E. coli* strain BL21 (DE3).

The present invention also relates to a method of producing a cellulase, which includes isolating and purifying the recombinant cellulase from a cell culture of the transformant.

The recombinant cellulase is preferably purified after the transformant is cultured by a conventional culturing method. The cellulase may be modified at a part of its amino acid sequence in any degree without an influence on cellulose decomposability depending on the base sequence of the insert introduced into the recombinant vector, that is, the encoding gene. The modification includes modification by deletion, insertion or substitution.

The present invention also relates to a reaction composition for decomposing cellulose including the recombinant cellulase.

Since the recombinant cellulase according to the present invention may digest cellulose in an endo or exo type, a monosaccharide can be formed. Accordingly, different from the conventional endoglucanase, which cannot degrade the cellulose into monomeric sugar, the use of recombinant cellulase in the present invention does not require an additional enzymatic saccharification process, contributing to the reduction in the process time and cost.

The present invention also relates to a method of decomposing cellulose, which includes reacting the recombinant cellulase with cellulose.

The reaction may be performed at pH 5 to 7 and 20 to 70° C., for example, 30 to 60° C., and specifically, pH 5.5 to 6.5 and 45 to 55° C., but the present invention is not particularly limited thereto.

Hereinafter, the present invention will be described in further detail with reference to examples according to the present invention, but the scope of the present invention is not limited to the following examples.

Example 1

Figure 1:
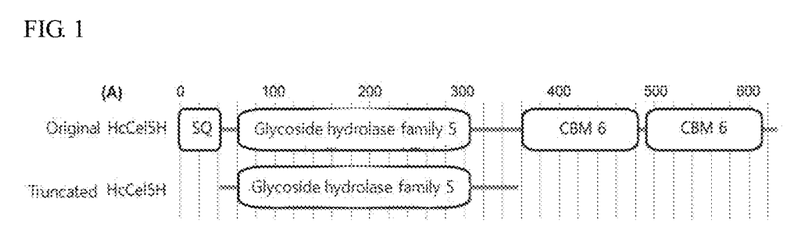
FIG. 1 is a schematic diagram of an architecture of recombinant HcCel5H (Truncated HcCel5H) constructed by removing two CBM6 domains from original HcCel5H.

Isolation and Purification of the Recombinant Cellulase According to the Present Invention Truncated HcCel5H (the recombinant cellulase according to the present invention) was prepared by removing a CBM6 domain from a Q2SFD8 (Gene ID: 3842516)-encoding base sequence (Hch03914) classified as an endoglucanase, which is a cellulase of *Hahella chejuensis* (FIG. 1).

A process of producing the recombinant cellulase according to the present invention will be described in further detail.

A genomic DNA of *Hahella chejuensis* KCTC 2396 was provided from Professor Kim Ji-hyun at Yonsei University (at that time, a doctor at the Korea Research Institute of Bioscience and Biotechnology). The genomic DNA was used in cloning as a template. As a cloning and protein expression host, *Escherichia coli* BL21 (DE3) was used.

The Q2SFD8 consisted of three main domains as described above, and for the experiment, primers were designed to produce two types of recombinant proteins: a protein not having a CBM6 domain sequence and a protein having a full domain sequence. Since the upstream region of the base sequence was shared, the same primer (F) was used, and a histidine (6×) sequence was attached to the downstream region of the base sequence to be isolated and purified with Histrap. Information on the primers is as follows.

Primers F and R1 were used for the cloning of a CBM6-removed protein, and primers F and R2 were used for the cloning of a protein having a full sequence. Restriction sites for BamHI (GGATCC) and NotI (GCGGCCGC) were added at the upstream and downstream regions, respectively.

```
Primer F:
                                        (SEQ ID NO: 3)
CCGGATCCATGCACGCTGTGCCGCCGTTATCG Primer R1:
                                        (SEQ ID NO: 4)
GGGCGGCCGCTCAGTGATGATGGTGATGGTGAGGAATGGGGTCGGAGCT

TTGGATAATG

Primer R2:
                                        (SEQ ID NO: 5)
GGGCGGCCGCTCAGTGATGATGGTGATGGTGTTTTTGTCCTTTAGTGAT

CTTGAACCAGTTCAGG
```

A PCR product was obtained using the primers prepared as described above and the template provided previously, and the fragment and a vector pET21a were digested with BamHI+NotI. The resultant products were subjected to gel elution, thereby obtaining fragments, and the fragments were ligased with a T4 ligase and then cloned with plasmids such as pET-HchCore and pET-HchFull, respectively.

Figure 2:
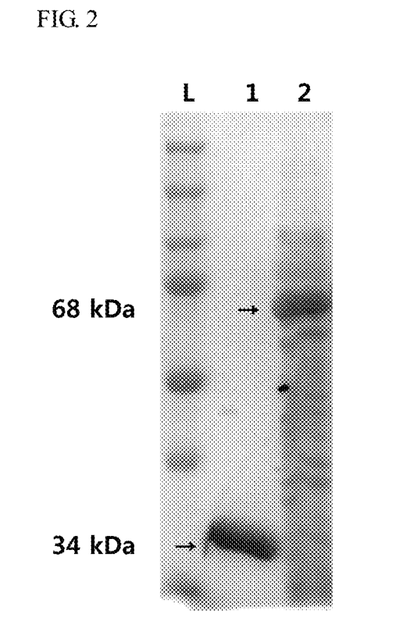
FIG. 2 is SDS-PAGE analysis for the original HcCel5H and the recombinant HcCel5H.

The recombinant plasmid was used to transform *E. coli* BL21 (DE3). The transformed *E. coli* was cultured in 2 L of a Luria-Bertani broth and grown at 37° C. and 200 rpm until an optical density of 600 nm reached 0.8, at which the temperature of culture medium was cooled to 16° C. Subsequently, the expression was induced with 0.5 mM IPTG Afterward, the resultant *E. coli* was further cultured for 16 hours and recovered to obtain only cells, and then the cells were mixed in a 20 mM Tris-Cl (pH 8.0) buffer to have a final volume of 40 ml. After a protease inhibitor, 1 mM PMSF, was added to the cells, the cells were disrupted by a sonic generator for 10 minutes. The resultant product was centrifuged again (16,000 rpm, 60 min) to remove a supernatant, which was then filtered with 0.45 nm PVDF, and loaded on a 5 ml Histrap (GE healthcare, USA). Afterward, the column was washed with a 20 mM Tris-Cl (pH 8.0) buffer in which 10 mM imidazole was dissolved to remove an unnecessary protein, and a 100 mM imidazole-added buffer was added to the above-described composition, thereby eluting the recombinant proteins. The purified proteins were separated by 10% SDS-PAGE at 180 V for 60 minutes to collect a high purity protein section, and then concentration and buffer exchange of the protein were carried out using Vivaspin 10000 (Satorious, USA). Afterward, the recombinant cellulase according to the present invention was obtained by loading the resultant protein on a SDS-PAGE gel again. A cellulase (original HcCel5H) having a total sequence, not a truncated form (recombinant HcCel5H), was also isolated and produced by the same process (FIG. 2). FIG. 2 shows an SDS-PAGE for the original HcCel5H and the recombinant HcCel5H (Lane L: protein marker; 1: truncated HcCel5H; 2: original HcCel5H). As shown in FIG. 2, it can be confirmed that the recombinant HcCel5H has a molecular weight of about 34 kDa.

Experimental Example 1

Figure 3:
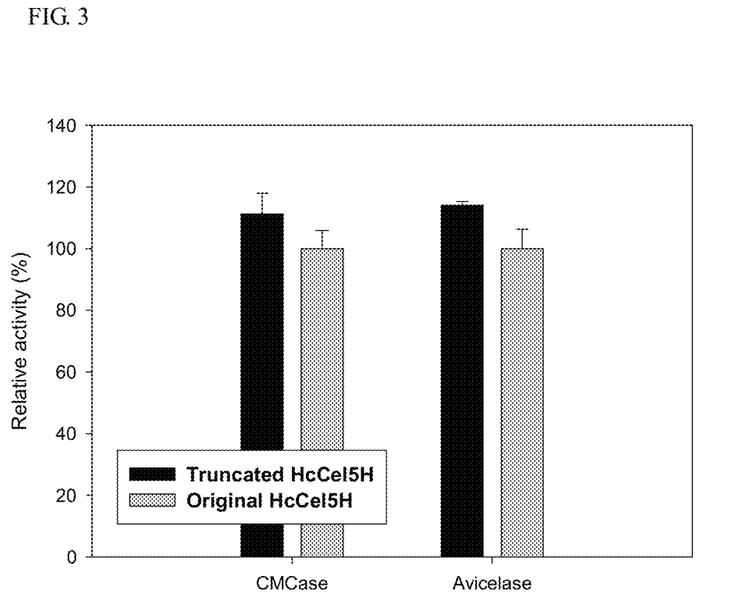
FIG. 3 shows a comparison of cellulolytic activities of the original HcCel5H and the recombinant HcCel5H with respect to soluble cellulose CMC and insoluble cellulose Avicel.

Comparison of Activities Between Original HcCel5H and Recombinant HcCel5H Depending on Substrate To compare the activities of original HcCel5H and recombinant HcCel5H, as a substrates, 1% CMC and 10% Avicel were used as soluble and insoluble celluloses, respectively, and the enzymatic reaction were performed in a total volume of 200 µl and at 50° C. Reaction times for CMC and Avicel were 20 minutes and 24 hours. Truncated HcCel5H and original HcCel5H were added at 0.1 mmol per g cellulose. The reaction mixture was boiled at 95° C. for 5 minutes to terminate the enzymatic activity, and the sugars produced from cellulose were quantified by DNS method. FIG. 3 shows a comparison for the activities of the original HcCel5H and the recombinant HcCel5H with respect to soluble cellulose, carboxy methyl cellulose (CMC), and insoluble cellulose, Avicel. As shown in FIG. 3, even though a cellulose binding domain family 6 was removed, it is seen that the activities were increased. Particularly, it can be seen that the activity of the cellulase designed herein with respect to the insoluble cellulose, Avicel, was similar to or higher than that of the original one. Considering that the molecular weight of the domain-free HcCel5H was half of the original one, it can be seen that the activity per the protein loading in terms of mass was increased by at least two times.

Experimental Example 2

CMCase Activity of Recombinant HcCel5H with Respect to pH

To determine the optimum pH of the recombinant HcCel5H prepared in Example 1, a CMCase activity of the recombinant HcCel5H depending on pH was measured using 1% CMC as a substrate in a total reaction amount of 200 µl for a reaction time of 20 minutes at a reaction temperature of 50° C. At pH 3 to 6, a sodium citrate buffer was used, at pH 7 to 8, a Tris-Cl buffer was used, and at pH 9, a glycerol-NaOH buffer was used. When the reaction was finished, the activity of the enzyme was blocked by boiling at 95° C. for 5 minutes, and quantified by a DNS method.

Figure 4:
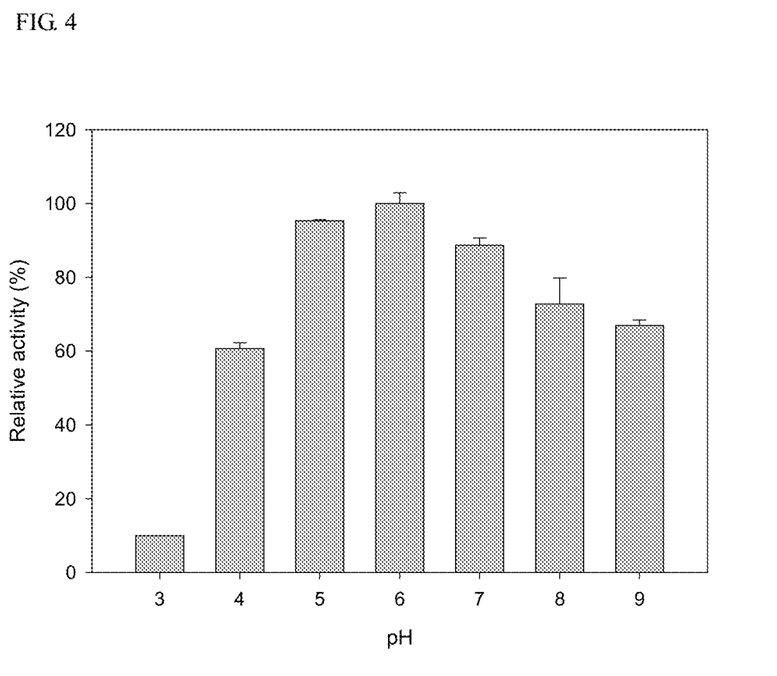
FIG. 4 shows CMCase activity of the recombinant HcCel5H with respect to pH.

FIG. 4 shows the CMCase activity of the recombinant HcCel5H with respect to pH. As shown in FIG. 4, the highest activity was shown at pH 6, and comparable activities were also shown at pH 5 and 7. Accordingly, it can be confirmed that the best reaction pH for the enzyme is pH 6.

Experimental Example 3

CMCase Activity of Recombinant HcCel5H with Respect to Temperature

To determine the optimum temperature of the recombinant HcCel5H prepared in Experimental Example 1, a temperature was measured using 1% CMC as a soluble substrate in a total reaction amount of 200 µl for a reaction time of 20 minutes at pH 6 in a 0.1M sodium citrate buffer. When the reaction was finished, the activity of the enzyme was blocked at 95° C. for 5 minutes, and quantified by a DNS method.

Figure 5:
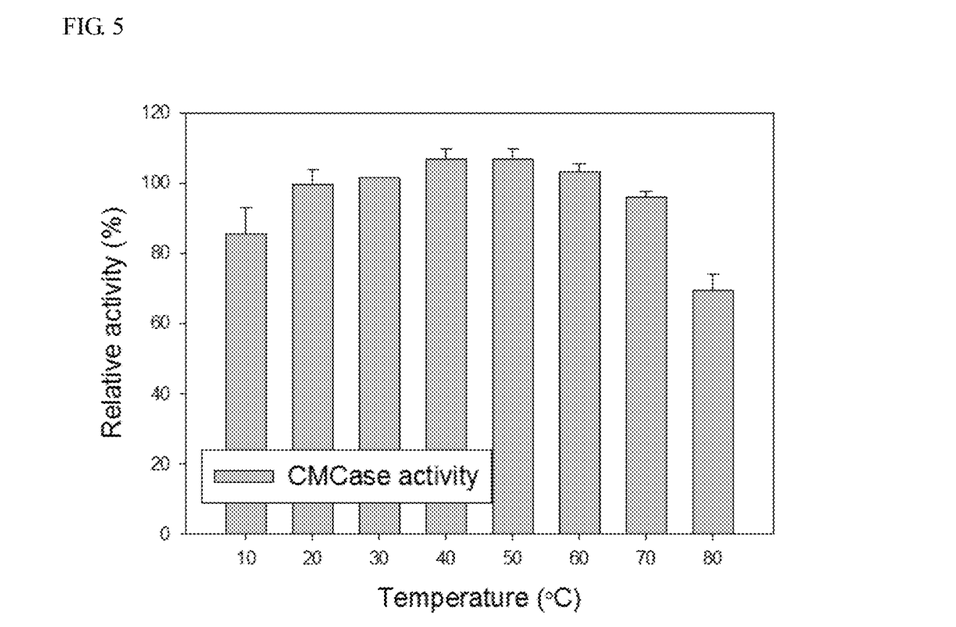
FIG. 5 shows CMCase activity of the recombinant HcCel5H with respect to temperature.

FIG. 5 shows the CMCase activity of the recombinant HcCel5H with respect to temperature. As shown in FIG. 5, it can be seen that the activity overall is shown in a considerably wide range. Particularly, the activity was almost similar at 20 to 70° C., and therefore it can be confirmed that a temperature range of the applied enzyme is considerably wide, and also confirmed that a reactivity is not decreased even at a high temperature (60° C. or higher).

Experimental Example 4

Avicelase Activity of Recombinant HcCel5H with Respect to Temperature

Activities were measured by temperature using insoluble cellulose, unlike Experimental Example 3. The activity was measured using an insoluble substrate, which was 10% Avicel, in a total reaction amount of 200 µl for a reaction time of 12 hours at pH 6 in a 0.1M sodium citrate buffer. When the reaction was finished, the activity of the enzyme was blocked by boiling at 95° C. for 5 minutes, and quantified by a DNS method.

Figure 6:
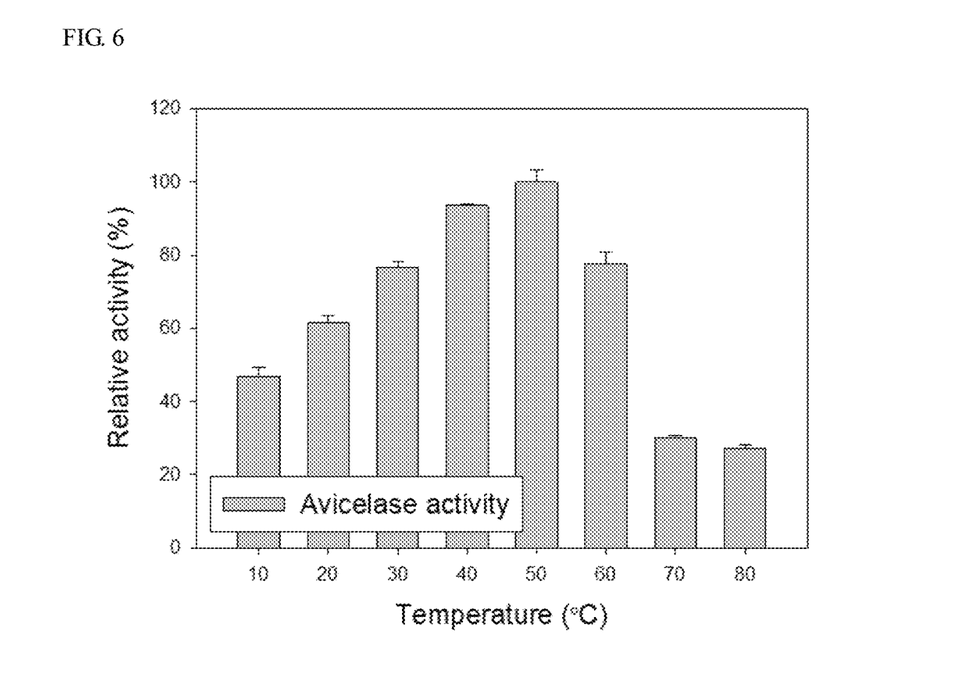
FIG. 6 shows Avicelase activity of the recombinant HcCel5H with respect to temperature.

FIG. 6 shows the Avicelase activity of the recombinant HcCel5H with respect to temperature. Since the reaction time was longer than that of FIG. 5, in FIG. 6, the highest activity was shown at 50° C. Particularly, even though *Hahella chejuensis*, which is the origin of the enzyme, is a marine microorganism, the highest activity was shown at a high temperature, for example, 50° C. It can be interpreted as the substrate-specific activity of cellulase. Moreover, the high activity at 50° C. indicates the cellulase has maintained its activity during the longer incubation time. Nonetheless, it can be confirmed that the recombinant HcCel5H shows a moderate activity even at 60° C., and thus has a tolerance to a high temperature.

Experimental Example 5

Temperature Stability Experiment for Recombinant HcCel5H

The amount of a protein was measured by Bradford analysis after incubation in different temperatures for 1 and 14 hours at pH 6 (0.1M sodium citrate). The protein stability was assessed by measuring the initial protein amount using Bradford assay, which was compared to the protein amount after incubation for a predetermined time at a varying temperature. The protein sample was collected by centrifugation at 16,000 rpm for 20 minutes. A supernatant was collected, and the amount of a protein was measured by the Bradford assay. The conservation of the protein stability may be seen by subtracting a later-measured value from the initially-measured value. The Bradford assay was performed by mixing 40 µl of a Bio-Rad protein assay dye reagent concentrate produced by Biorad with 160 µl of a diluted protein for 5 minutes at 30° C., and an absorbance was measured at a wavelength of 595 nm using a microassay reader to deduce a result. As a standard material, 10 mg of bovine serum albumin (BSA) was used. That is, an absorbance value of the protein sample obtained in a calibration curve from the standard material was calculated, and a difference from the actual concentration of the protein may be calculated.

Figure 7:
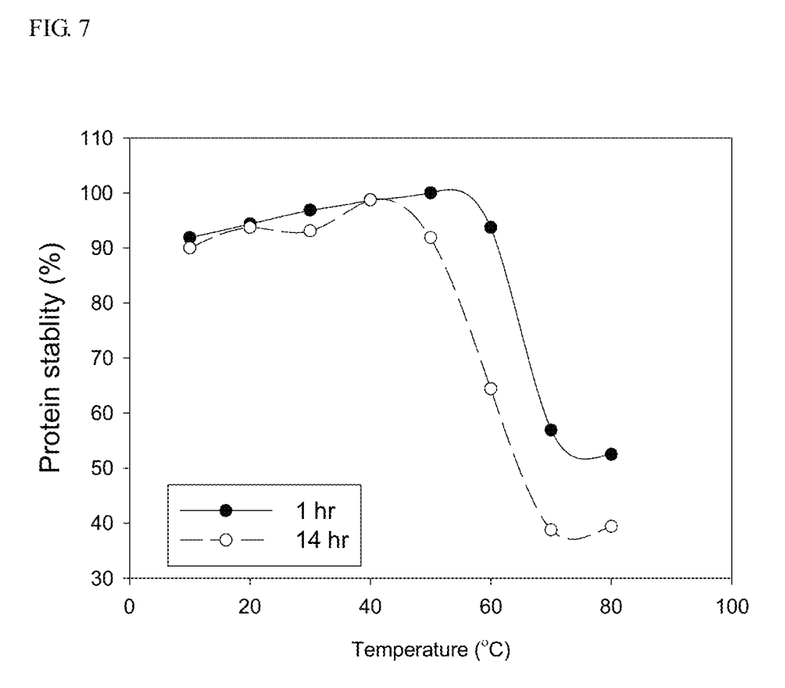
FIG. 7 is an experimental result showing a temperature stability of the recombinant HcCel5H.

FIG. 7 is an experimental result showing temperature stability of the recombinant HcCel5H. FIG. 7-supports the interpretations on FIGS. 5 and 6 performed previously. First, when the reaction was carried out at each temperature, there was no difference in stability until 60° C. Also, at 70° C., the stability was decreased by half, but according to the result of FIG. 5, it was confirmed that the activity was good at a high temperature. When incubated for 14 hours, it can be seen that the stability was greatly decreased at 60° C., but a heat tolerance was uniformly maintained until 50° C., and such a result supports that the optimum activity of FIG. 6 is 50° C. Also, at 30° C. and 60° C., compared to an active-type protein, the recombinant HcCel5H shows a higher activity at 60° C., which is the result of demonstrating again that the activity is high at a high temperature.

Experimental Example 6

Analysis for Reaction Product of Recombinant HcCel5H Using Avicel as a Substrate To confirm a type of a reaction product produced by the recombinant HcCel5H, 10% Avicel was used as a substrate, and a reaction was performed under conditions of a total reaction amount of 200 µl, 50° C., pH 6, and a 0.1M sodium citrate buffer. The reaction products was sampled with respect to time, and analyzed by (a) DNS and (b) thin liquid chromatography (TLC), respectively.

The DNS analysis was performed by the same method as in the examples. In the TLC analysis, a mixture of butanol: acetic acid:water at a ratio of 2:1:1 was used as a developing solution, and a TLC plate was covered with silica. After development, 10% sulfate-containing ethanol was sprayed and dried, and a color reagent was sprayed and dried again. Afterward, coloring was confirmed by applying heat.

Figure 8:
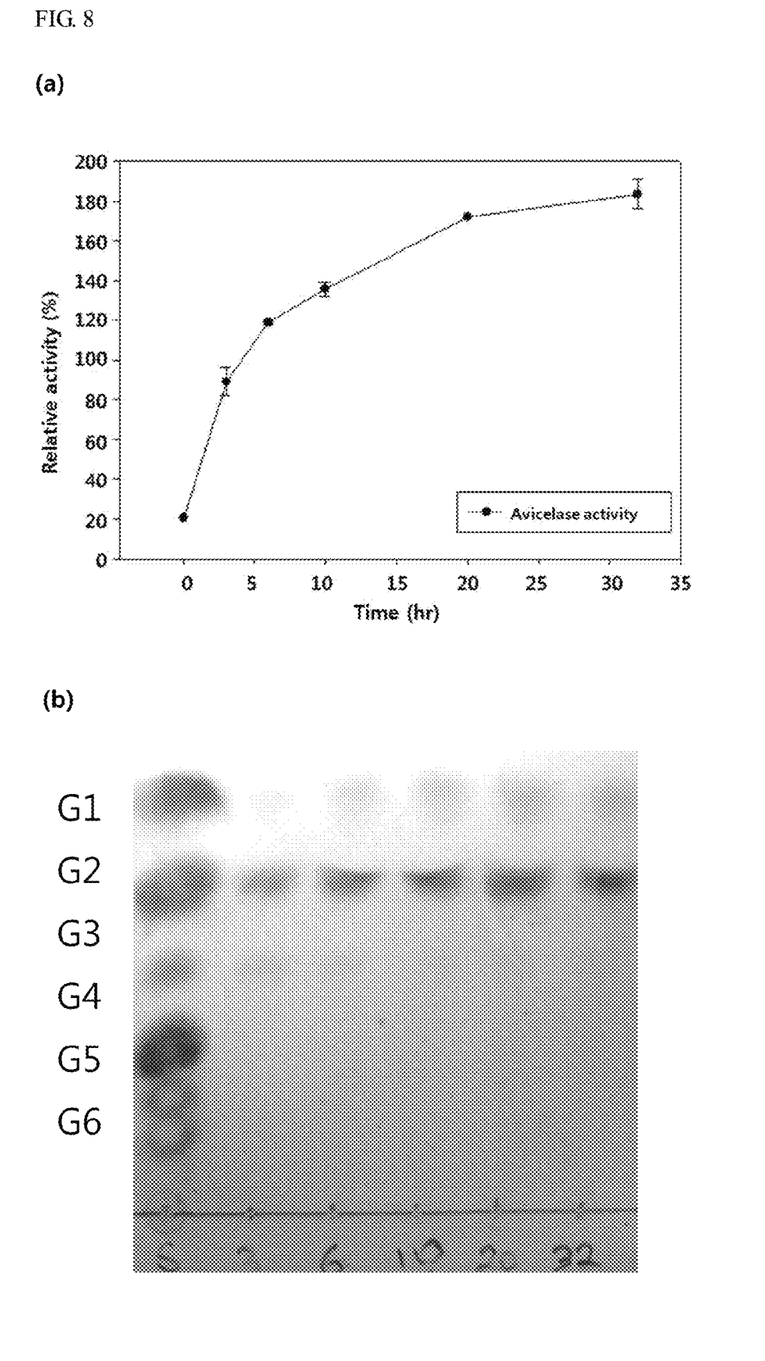
FIG. 8 shows (a) DNS and (b) TLC results for reaction products of the recombinant HcCel5H using Avicel as a substrate with respect to time.

FIG. 8 shows the results obtained by analyzing a reaction product of the recombinant HcCel5H by time using Avicel as a substrate through (a) DNS and (b) TLC. As shown in FIG. 8a, it can be seen that the reaction product is gradually saturated as the reaction progresses. However, when each section is confirmed in FIG. 8b, it was confirmed that glucose, cellobiose and cellotriose patterns are changed. It can be confirmed that, first, formed reaction products were mainly cellobiose and cellotriose, but as time progresses there is no change in cellobiose, and production of glucose formed by decomposing the cellotriose is greatly increased.

Experimental Example 7

Analysis for Reaction Product of Recombinant HcCel5H Using Oligosaccharide as Substrate To confirm a type of an oligosaccharide capable of being decomposed by the recombinant HcCel5H, 1% oligosaccharide was used as a substrate, and a reaction was performed under conditions of a total reaction amount of 20 µl, 50° C., pH 6, and a 0.1M sodium citrate buffer for 20 minutes. The resultant products were analyzed by thin liquid chromatography (TLC). An analysis method is the same as described in Experimental Example 6.

Figure 9:
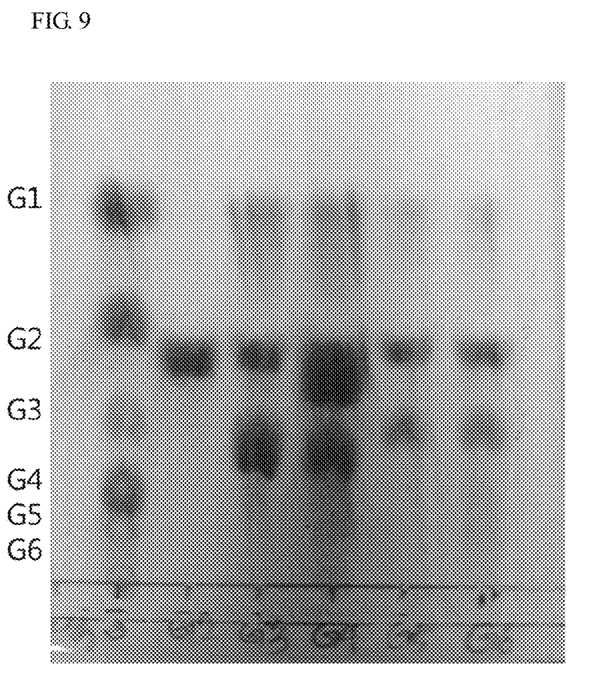
FIG. 9 is a TLC result for a reaction product of the recombinant HcCel5H using oligomers as substrates.

The high processivity of the cellulase, which was confirmed in FIG. 8, was also confirmed in this experimental example. In FIG. 9, to more specifically examine the type capable of being decomposed by HcCel5H, cellobiose (G2), cellotriose (G3), cellotetraose (G4), cellopentaose (G5), and cellohexaose (G6) were used in a reaction as a substrate. According to the result shown in FIG. 9, since the cellobiose was not decomposed, the cellulase of the present invention was found not to be β-glucosidase. Also, since a product is mainly the cellobiose (G2) and a pattern of gradually decomposing the cellotriose (G3) to the glucose (G1) is observed, it can be seen that the enzyme has the property of an exocellulase. Originally, it is common that a processive exocellulase does not decompose a substrate such as CMC, but the enzyme has previously shown a high activity as the endocellulase for CMC in FIGS. 1 and 2. As a result, the enzyme may be classified as a processive cellulase having both of the endo and exo functions. The cellulase of the present invention has significances in that such a type of enzyme is very rarely observed in bacteria, and has a high activity. Also, due to the activity exhibited even at a high temperature, the enzyme is also very useful in an industrial saccharification process.

Experimental Example 8

Enzyme Kinetic Study on Soluble Cellulose, Carboxyl Methyl Cellulose (CMC), and Insoluble Cellulose, Avicel Determination of an enzyme kinetics constant in an experiment by the Michaelis-Menten equation was used since the Michaelis-Menten equation is a general method of obtaining the kinetic constant of an enzyme. Table 1 shows the Michaelis constant $K_m$, the maximum velocity $V_{max}$ and the catalytic constant $K_{cat}$, obtained from the experiment. Table 1 shows precisely quantified and objectified data of actual reaction patterns between the recombinant cellulase and a substrate. An experimental method is as follows. In consideration of the initial reaction rate, various substrate concentrations from 1 to 4% (w/v) with respect to CMC were used, to which 0.1 nmol of the same recombinant cellulase was added to each sample, and a reaction time was 5 minutes. For Avicel, various substrate concentrations from 0.8 to 4% (w/v) were used, to which 0.5 nmol of the recombinant cellulase was added to each sample, and the reaction time was 2 hours. As a reaction solution, 200 µl of 50 mM sodium citrate (pH 6.0) was used and allowed to react at 50° C. From the double reciprocal plot called the Lineweaver Bulk plot using the experimental data obtained above, $K_m$, $K_{cat}$, and $K_{cat}$ values were calculated.

Rapid decomposition when the substrate having the lowest Michaelis constant $K_m$, CMC, was used, demonstrates that the property of the endoglucanase is predominantly exhibited. However, unlike a general cellulase, the recombinant cellulase shows a relatively high activity even in the use of Avicel, and therefore it was also concluded that the recombinant cellulase also has the property of the exoglucanase. The great difference in decomposability depending on a substrate is caused by the property of a substrate such as much greater enzyme accessibility for the soluble substrate, not by the original property of the enzyme itself.

TABLE 1

| Substrate | Enzyme | $K_m$ (mg · ml$^{-1}$) | $V_{max}$ (mg · ml$^{-1}$ · min$^{-1}$) | $K_{cat}$ (min$^{-1}$) |
|---|---|---|---|---|
| CMC | HcCel5H | 21.34 | $1.67 \times 10^{-1}$ | $9.76 \times 10^{-1}$ |
| Avicel | | 171.77 | $4.94 \times 10^{-3}$ | $2.89 \times 10^{-3}$ |

Experimental Example 9

Confirmation of High Processivity 0.2 nmol of the recombinant cellulase HcCel5H was added to a substrate such as a 10 mg filter paper (Whatman No 1.). Here, a reaction solution was 200 µl of a 50 mM sodium citrate buffer (pH 6.0), and a reaction was carried out at 50° C. for 2 hours. To detect a soluble sugar, a supernatant was obtained, and reducing sugars were measured by DNS. To detect an insoluble sugar, a remaining filter paper was washed six times, and the insoluble sugar was detected by a BCA analysis. When the soluble sugar value is divided by the insoluble sugar value, the processivity of the recombinant cellulase may be measured. Accordingly, it can be noted that the cellulase having a high reactivity processively degrades substrates, and thus has a far higher content of the soluble sugar than the general cellulase, and as shown in Table 2, the recombinant enzyme has a high processive reactivity, for example, 5.78 (the processive reactivity of a general cellulase is 2 to 3).

TABLE 2

| Enzyme | Level of processive reactivity | % soluble sugar | % insoluble sugar |
|---|---|---|---|
| HcCel5H | 5.78 ± 0.78 | 85.16 | 14.84 |

Experimental Example 10

Confirmation of Activity of Recombinant HcCel5H Using Viscometer

Figure 10:
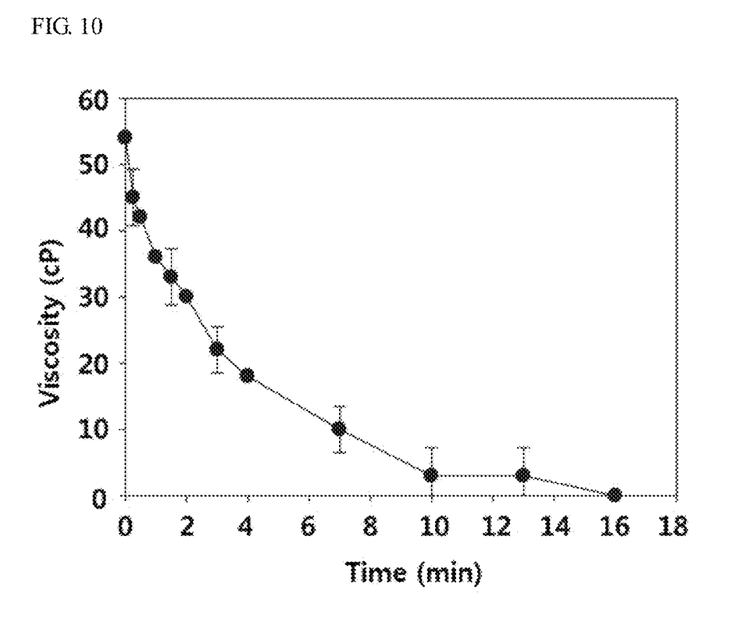
FIG. 10 is an experimental result showing an influence of the activity of the recombinant HcCel5H on the viscosity of a CMC solution.

The activity of the recombinant HcCel5H was further confirmed using a viscometer. The viscometer used was DV-II+ Pro Extra (Brookfield, Middleboro, Mass., USA), and the activity was measured by detecting a viscosity value (Cp) decreased over time. A liquid solution was prepared by dissolving CMC in 25 ml of a 0.1 M sodium citrate buffer (pH 6.0) to have a concentration of 3% (w/v). 0.1 nmol of the recombinant HcCel5H was added to the liquid solution at room temperature, 30 ml of the liquid solution was poured in the viscometer, and a change in viscosity was observed while rotating the viscometer. FIG. 10 shows that the viscosity is decreased to 0 in 20 minutes by the above-described procedure. This is a typical property of the endoglucanase, which makes it reconfirmed that the recombinant HcCel5H having the property of the exoglucanase shown in FIGS. 8 and 9 while simultaneously having an obvious property of the endoglucanase. As a result, it was determined that the recombinant HcCel5H is not simply an endo or exoglucanase, but a high reactivity cellulase having both of the properties of the endo and exoglucases.

The invention claimed is:

1. A recombinant cellulase produced by removing a signal sequence and two CBM6 domains from a *Hahella chejuensis*-derived cellulase (HcCel5H).

2. The recombinant cellulase of claim 1, which has the amino acid sequence set forth in SEQ ID NO: 1 in the sequence listing.

3. The recombinant cellulase of claim 1, which simultaneously has activities of an endoglucanase and an exoglucanase.

4. The recombinant cellulase of claim 1, which decomposes a cellotriose or higher oligosaccharide.

5. A gene encoding the cellulase of claim 1.

6. The gene of claim 5, which has the nucleic acid sequence set forth in SEQ ID NO: 2.

7. A recombinant vector expressing the cellulase of claim 1.

8. A transformant transformed with the recombinant vector of claim 7.

9. A method of producing a cellulase, comprising:
isolating and purifying the recombinant cellulase from a cell culture of the transformant of claim 8.

10. A method of decomposing cellulose, comprising:
reacting the cellulase of claim 1 with cellulose.

11. The method of claim 10, wherein the reaction is carried out at pH of 5.5 to 6.5 and 45 to 55° C.

* * * * *

```
SEQUENCE LISTING

<160> NUMBER OF SEQ ID NOS: 5

<210> SEQ ID NO 1
<211> LENGTH: 307
<212> TYPE: PRT
<213> ORGANISM: Artificial Sequence
<220> FEATURE:
<223> OTHER INFORMATION: Truncated HcCel5H

<400> SEQUENCE: 1

Met His Ala Val Pro Pro Leu Ser Val Gln Gly Asn Lys Val Val Ser
1               5                   10                  15

Gly Gly Gln Gln Val Ser Leu Gly Gly Asn Ser Leu Phe Trp Ser Asn
            20                  25                  30

Asn Gly Trp Gly Gly Glu Arg Phe Tyr Asn Ser Gly Ala Val Gly Ala
        35                  40                  45

Ile Lys Asn Asp Trp Lys Ser Ser Ile Val Arg Ala Ala Met Gly Val
    50                  55                  60

Asp Glu Gly Gly Gly Tyr Leu Gln Asp Arg Glu Gly Asn Arg Asn Lys
65                  70                  75                  80

Val Ile Ser Val Val Asp Ala Ala Ile Ala Asn Asp Met Tyr Val Ile
                85                  90                  95

Ile Asp Trp His Ser His His Ala His Gln Tyr Lys Asn Glu Ala Ile
            100                 105                 110

Glu Phe Phe Gln Asp Met Ala Arg Arg Tyr Gly Asp Lys Asn Asn Val
        115                 120                 125

Ile Tyr Glu Val Tyr Asn Glu Pro Leu Asp Val Ser Trp Ser Gly Val
130                 135                 140

Ile Lys Pro Tyr Ala Glu Ala Val Ile Asp Ala Ile Arg Gln Val Asp
145                 150                 155                 160

Pro Asp Asn Leu Ile Ile Val Gly Thr Arg Gln Trp Ser Gln Glu Val
                165                 170                 175

Glu Glu Ala Ser Trp Asp Pro Ile Arg Lys Asn Asn Ile Ala Tyr Thr
            180                 185                 190

Leu His Phe Tyr Ala Gly Thr His Lys Gln Trp Leu Arg Asp Lys Ala
        195                 200                 205

Gln Asn Ala Met Asn Asn Gly Ile Ala Leu Phe Val Thr Glu Trp Gly
    210                 215                 220
```

```
Thr Val Asp Ala Ser Gly Asp Gly Ala Val Asn Glu Ser Glu Thr Trp
225                 230                 235                 240

Ala Trp Val Asp Phe Met Arg Asn His Gly Ile Ser His Ala Asn Trp
            245                 250                 255

Ala Leu Asn Asp Lys Ala Glu Gly Ala Ser Thr Phe Trp Pro Gly Ala
        260                 265                 270

Ser Gly Thr Gly Gly Trp Asn Asp Gly Asn Leu Thr Pro Ser Gly Lys
    275                 280                 285

Leu Val Lys Ser Ile Ile Gln Ser Ser Asp Pro Ile Pro His His His
    290                 295                 300

His His His
305
```

<210> SEQ ID NO 2
<211> LENGTH: 924
<212> TYPE: DNA
<213> ORGANISM: Artificial Sequence
<220> FEATURE:
<223> OTHER INFORMATION: Truncated HcCel5H

<400> SEQUENCE: 2

```
atgcacgctg tgccgccgtt atcggtgcag ggcaataaag tcgtcagtgg cggtcagcaa       60
gtcagtctgg gaggcaacag cctgttttgg agcaacaacg gctggggagg ggagcgcttt      120
tataattccg gcgcggtagg ggccatcaaa aacgactgga agtccagcat tgtgcgggcc      180
gccatggggg tggatgaagg cggcggatat ttacaggacc gggaaggcaa ccgtaataaa      240
gtcatctccg tggtggacgc cgccatcgcc aatgatatgt acgtcatcat cgactggcac      300
tcccaccatg ctcatcagta caagaacgaa gccatcgagt ttttccagga catggcgcgc      360
cgctacggcg ataaaaacaa tgttattac gaagtctata cgagccgct ggatgtgtcc       420
tggagcggcg ttatcaagcc ctacgccgag gcggtgattg acgctatccg ccaagttgat      480
ccagataacc tgatcattgt cgggactcgc caatggtcgc aggaagtgga ggaagcctcc      540
tgggacccta tccgcaagaa caatatcgcc tatacgctgc attttacgc cggcacgcat       600
aagcagtggc tgcgcgacaa agcgcaaaac gccatgaaca acggcatcgc acttttcgtg      660
acggagtggg gaaccgtaga cgccagcggc gatggcgcgg ttaatgaaag tgaaacctgg      720
gcctgggtcg acttcatgcg caaccacggc atcagccacg ccaactgggc gctgaatgat      780
aaagccgaag cgcctcaac gttctggcct ggggctagtg gaaccggtgg ttggaatgat       840
ggaaacctga cgccttccgg taaactggtg aaatccatta tccaaagctc gaccccatt      900
cctcaccatc accatcatca ctga                                             924
```

<210> SEQ ID NO 3
<211> LENGTH: 32
<212> TYPE: DNA
<213> ORGANISM: Artificial Sequence
<220> FEATURE:
<223> OTHER INFORMATION: Primer F

<400> SEQUENCE: 3

```
ccggatccat gcacgctgtg ccgccgttat cg                                     32
```

<210> SEQ ID NO 4
<211> LENGTH: 59
<212> TYPE: DNA
<213> ORGANISM: Artificial Sequence
<220> FEATURE:
<223> OTHER INFORMATION: Primer R1

```
<400> SEQUENCE: 4
gggcggccgc tcagtgatga tggtgatggt gaggaatggg gtcggagctt tggataatg        59

<210> SEQ ID NO 5
<211> LENGTH: 65
<212> TYPE: DNA
<213> ORGANISM: Artificial Sequence
<220> FEATURE:
<223> OTHER INFORMATION: Primer R2

<400> SEQUENCE: 5
gggcggccgc tcagtgatga tggtgatggt gtttttgtcc tttagtgatc ttgaaccagt        60
tcagg                                                                    65
```